United States Patent
Hu et al.

(10) Patent No.: US 8,634,077 B2
(45) Date of Patent: Jan. 21, 2014

(54) METHODS AND SYSTEMS FOR OPTICALLY CHARACTERIZING A TURBID MATERIAL USING A STRUCTURED INCIDENT BEAM

(75) Inventors: Xin-Hua Hu, Greenville, NC (US); Cheng Chen, Greenville, NC (US)

(73) Assignee: East Carolina University, Greenville, NC (US)

(*) Notice: Subject to any disclaimer, the term of this patent is extended or adjusted under 35 U.S.C. 154(b) by 214 days.

(21) Appl. No.: 13/122,062

(22) PCT Filed: Oct. 1, 2009

(86) PCT No.: PCT/US2009/059174
§ 371 (c)(1), (2), (4) Date: Aug. 11, 2011

(87) PCT Pub. No.: WO2010/039921
PCT Pub. Date: Apr. 8, 2010

(65) Prior Publication Data
US 2011/0286000 A1   Nov. 24, 2011

Related U.S. Application Data

(60) Provisional application No. 61/101,762, filed on Oct. 1, 2008.

(51) Int. Cl.
*G01N 21/55* (2006.01)
(52) U.S. Cl.
USPC .......................................... 356/445; 356/446
(58) Field of Classification Search
USPC ................................. 356/445–446
See application file for complete search history.

(56) References Cited

U.S. PATENT DOCUMENTS

| | | |
|---|---|---|
| 3,960,449 A | 6/1976 | Carleton et al. |
| 4,293,221 A | 10/1981 | Kay et al. |
| 4,500,641 A | 2/1985 | Van den Engh et al. |

(Continued)

FOREIGN PATENT DOCUMENTS

| | | |
|---|---|---|
| CN | 1511299 A | 7/2004 |
| CN | 1685226 A | 10/2005 |

(Continued)

OTHER PUBLICATIONS

Chen, C. et al., "Numerical study of reflectance imaging using a parallel Monte Carlo Method", Med. Phys 2007, vol. 34, No. 7 pp. 2939-2948, Jul. 31, 2007.

(Continued)

*Primary Examiner* — Tarifur Chowdhury
*Assistant Examiner* — Isiaka Akanbi
(74) *Attorney, Agent, or Firm* — Myers Bigel Sibley & Sajovec PA

(57) ABSTRACT

Methods and systems for optically characterizing a turbid sample are provided. A structured light beam is impinged on the sample. The sample includes an embedded region. A reflected light image of the structured light beam is detected from the sample. A measured reflectance image of the structured light beam for the sample is determined based on the reflected light image and a reflectance standard. The following parameters are determined: absorption coefficients ÿa, scattering coefficient ÿs and anisotropy factor g of the sample from the reflectance image. A size parameter of the embedded region is estimated based on the absorption coefficients ÿa, scattering coefficient ÿs and/or anisotropy factor g of the sample from the measured reflectance image.

19 Claims, 6 Drawing Sheets

(56) References Cited

U.S. PATENT DOCUMENTS

| | | | |
|---|---|---|---|
| 5,017,497 | A | 5/1991 | De Grooth et al. |
| 5,308,990 | A | 5/1994 | Takahashi et al. |
| 5,416,582 | A | 5/1995 | Knutson |
| 5,929,443 | A | 7/1999 | Alpano |
| 6,011,626 | A * | 1/2000 | Hielscher et al. ............. 356/367 |
| 6,760,609 | B2 * | 7/2004 | Jacques ......................... 600/331 |
| 7,106,972 | B2 * | 9/2006 | Alfano et al. .................. 398/158 |
| 7,127,109 | B1 | 10/2006 | Kim et al. |
| 7,289,211 | B1 * | 10/2007 | Walsh et al. ................... 356/369 |
| 7,818,154 | B2 * | 10/2010 | Palmer et al. ..................... 703/11 |
| 7,920,252 | B2 * | 4/2011 | Hu .................................. 356/73 |
| 7,960,707 | B2 * | 6/2011 | Hall et al. .................. 250/459.1 |
| 2002/0141625 | A1 | 10/2002 | Nelson |
| 2005/0110996 | A1 | 5/2005 | Sharpe et al. |
| 2007/0133002 | A1 | 6/2007 | Wax et al. |
| 2007/0158585 | A1 * | 7/2007 | Hall et al. .................. 250/458.1 |
| 2010/0042005 | A1 * | 2/2010 | Bigio et al. ................... 600/476 |
| 2013/0165798 | A1 * | 6/2013 | Bigio et al. ................... 600/476 |

FOREIGN PATENT DOCUMENTS

| | | |
|---|---|---|
| EP | 0 061 809 | 10/1982 |
| EP | 1707944 A2 | 10/2006 |
| WO | WO 98/34094 | 8/1998 |
| WO | WO 2004/017041 A2 | 2/2004 |
| WO | WO 2009/151610 | 12/2009 |

OTHER PUBLICATIONS

Chen, C. et al., "A primary method for determination of optical parameters of turbid samples and application to intralipid between 550 and 1630nm", Optics Express 2006, vol. 14, No. 16, pp. 7420-7435, Aug. 7, 2006.

Yuan Cao-Jin et al; "Three-dimensional surface contouring of reflecting micro-object by digital holography with short-coherence light source"; Acta Physica Sinica vol. 56, No. 1, Jan. 2007 Chin. Phys. Soc. pp. 218-223.

International Search Report and Written Opinion for PCT/US2009/059174, mailed May 10, 2010, 11 pages.

International Preliminary Report on Patentability for PCT/US2009/059174, mailed Apr. 14, 2011, 6 pages.

International Search Report and Written Opinion for PCT/US2009/003508, mailed Jan. 19, 2010, 11 pages.

International Preliminary Report on Patentability for PCT/US2009/003508, mailed Dec. 23, 2010.

* cited by examiner

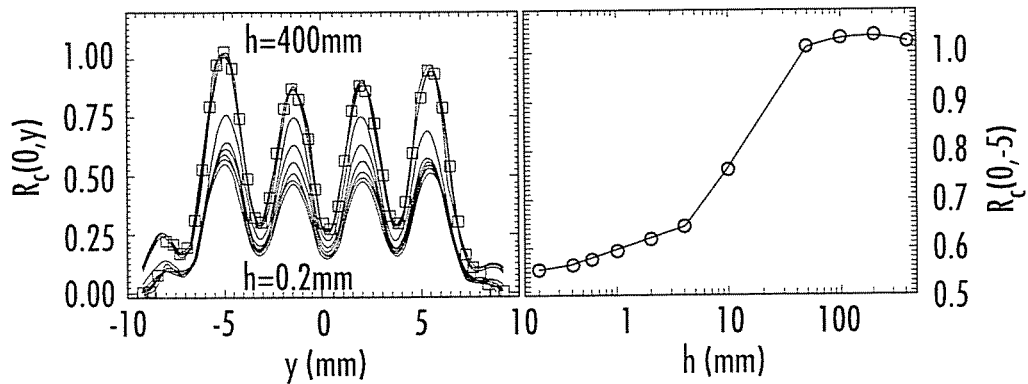
FIG. 2A   FIG. 2B
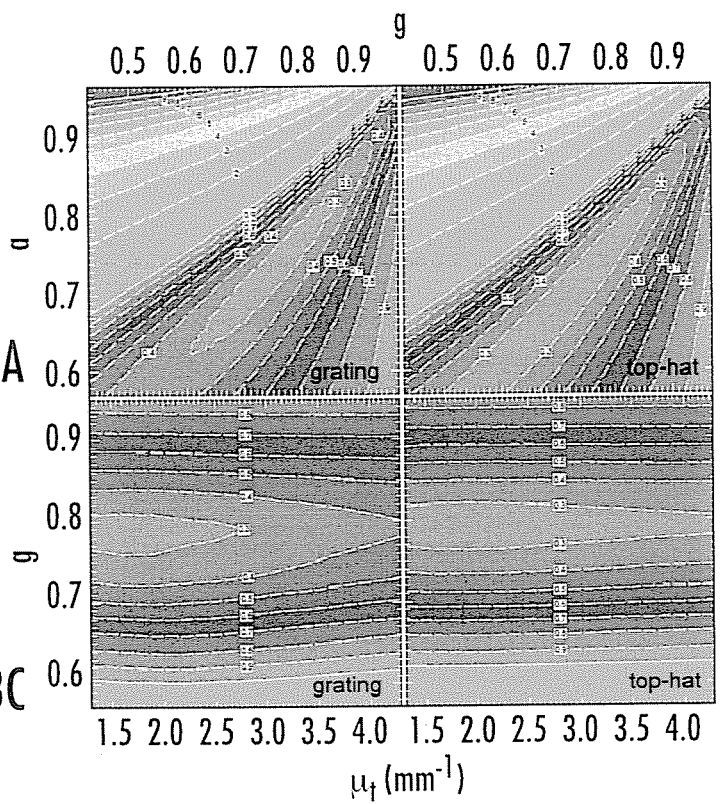
FIG. 3A   FIG. 3B
FIG. 3C   FIG. 3D

US 8,634,077 B2

METHODS AND SYSTEMS FOR OPTICALLY CHARACTERIZING A TURBID MATERIAL USING A STRUCTURED INCIDENT BEAM

RELATED APPLICATIONS

The present application is a 35 U.S.C. §371 national phase application of PCT International Application No. PCT/US2009/059174 having an international filing date of Oct. 1, 2009, claiming priority to U.S. Provisional Application Ser. No. 61/101,762 filed Oct. 1, 2008. The disclosures of each application are incorporated herein by reference in their entireties. The above PCT International Application was published in the English language as International Publication No. WO 2010/039921 A2.

FIELD OF THE INVENTION

The present invention relates to methods and systems for optically characterizing a turbid material based on an absorption coefficient, scattering coefficient and/or anisotropy factor.

BACKGROUND

Quantitative characterization of turbid media has been pursued intensely with a limited number of reflected light signals to determine optical parameters (1, 2). Achieving the same goal with reflectance image data, potentially consisting of 10,000 or more signals, remains a challenging problem despite its potentials for noninvasive detection and diagnosis (3). Optical characterization of turbid media can have wide-ranged applications to materials analysis in industry, lesion diagnosis in medicine and biological and chemical research but requires accurate models of light interaction with turbid media. For example, the radiative transfer theory is generally regarded as the most accurate optical model and uses three optical parameters to characterize a material: $\mu_a$ (absorption coefficient), $\mu_s$ (scattering coefficient) and g (anisotropy factor). However, the problems formulated on the basis of radiative transfer theory can be difficult to solve analytically without introducing various approximations.

One approximation of the radiative transfer theory is the diffusion model for photon transport. The diffusion model is an approximation of the radiative transfer theory in which all measured light is assumed to be scattered or "diffused." The diffusion model is not as accurate as the radiative transfer model; however, the diffusion model can be used to determine $\mu_a$ and $\mu_s'$ (reduced scattering coefficient=$\mu_s(1-g)$). One potential advantage of using the diffusion model is that the results of the calculation are independent of the values of $\mu_s$ and g as long as $\mu_s'$ remains the same. This can be referred to as the similarity principle. If the reflected light signals are dominated by the multiply scattered light, then the diffusion model may be relatively accurate. Therefore, the diffusion model and similarity principle can be applied with a sufficient degree of accuracy to the cases of large source-detector distances or materials with a relatively large ratio of $\mu_s$ to $\mu_a$ or to small values of g.

A noninvasive method of spatially resolved diffuse reflectance (SRDR) has been used extensively to determine $\mu_a$ and $\mu_s'$ based on a diffusion model of reflectance signals measured with either continuous-wave (cw) or frequency modulated light (13-15). In this method a "point" source of scattered light is introduced into the sample at a small spot either through an optical fiber in contact with a sample or in the form of an incident beam focused at the sample surface. Reflected light signals are acquired at multiple locations of different source-detector distances (2, 16). The SRDR method could be implemented with an imager to replace the single detectors for non-contact acquisition of the reflectance signals through pixel binning (17-19). Further refinement of the image-based SRDR method was reported recently to separate $\mu_s$ and g from $\mu_s'$, determined through a diffusion model, through the Monte Carlo simulations of a second reflectance image acquired with a focused beam of oblique incidence (20). Despite these improvements, however, the use of the diffusion model in the SRDR method often introduces errors in the inversely determined optical parameters if the signals are not dominated by multiply scattered light such as the cases of short source-detector distances and/or with samples of small a and/or large g. Furthermore, the SRDR method does not fully take the advantage of imaging, methods which favor full-field illumination since the pixel readings of an imager are of limited dynamic ranges in comparison to the single detectors. Finally, conventional methods of reflectance measurements, including the SRDR method, are generally not able to characterize heterogeneous turbid materials in which the optical parameters vary in different regions, such as in the case where one material is embedded in another material.

Optical fibers have been used in the SRDR methods to detect reflectance signals from a sample media. For example, U.S. Patent Publication No. 20060247532 to Ramanujam proposes an iterative process that determines the absorption and scattering coefficients of tissue from a set of diffuse reflectance measurements made with an optical spectrometer operating in the UV-VIS spectral range and using optical fibers to detect reflected light signals. The relationship between measured diffuse reflectance and the absorption and scattering coefficients is modeled using a Monte Carlo simulation based on a similarity principle to increase the speed of the simulation. However, this approach only determines $\mu_a$, and $\mu_s'$ rather than $\mu_a$, $\mu_s$ and g.

In addition, the use of optical fibers in light detection can be prone to measurement errors because the fiber probes generally require direct contact with the sample medium. Furthermore, the optical fiber techniques discussed above may be limited to samples with homogeneous or homogeneously layered structures. Therefore, optical fiber detection of reflected light signals has limited usefulness especially in heterogeneous samples.

SUMMARY OF EMBODIMENTS OF THE INVENTION

According to embodiments of the present invention, methods for optically characterizing a turbid sample are provided. A structured light beam is impinged on the sample. The sample includes an embedded region. A reflected light image of the structured light beam is detected from the sample. A measured reflectance image of the structured light beam for the sample is determined based on the reflected light image and a reflectance standard. The following parameters are determined: absorption coefficient $\mu_a$, scattering coefficient $\mu_s$ and anisotropy factor g of the sample from the reflectance image. A size parameter of the embedded region is estimated based on the absorption coefficient $\mu_a$, scattering coefficient $\mu_s$ and/or anisotropy factor g of the sample from the measured reflectance image.

In some embodiments, the measured reflectance image is determined by dividing the reflected light image by a maximum pixel illumination of the reflectance standard. The reflectance standard can be a calibrated diffuse reflectance standard. In particular embodiments, the illumination is provided by an incoherent, full-field light beam.

In some embodiments, the embedded region comprises a tissue abnormality, and the size parameter of the embedded region is correlated to a likelihood of cancer malignancy. The tissue abnormality can be an epithelial abnormality, and the size parameter is a depth of the epithelial abnormality.

In some embodiments, the structured, incoherent light beam is formed by passing an incoherent light beam through a stencil having transmissive and non-transmissive or partially transmissive regions to thereby foun a structured profile. The structured profile can be a grating pattern.

In some embodiments, the measured reflectance image is detected by a detector that is spaced-apart from the sample.

In some embodiments, determining the absorption coefficient $\mu_a$, scattering coefficient $\mu_s$ and anisotropy factor g of the sample from the reflectance image is based on a Monte Carlo simulation of radiative transfer theory and/or an optical diffusion model.

According to further embodiments of the present invention, a system for optically characterizing a turbid sample includes a light source configured to impinge a structured light beam on a sample. The sample comprises an embedded region. A detector is configured to detect a reflected light image of the sample illuminated by the structured light beam. A signal analyzer is configured to determine a measured reflectance image of the structured light beam for the sample based on the reflected light image and a reflectance standard, to determine an absorption coefficients $\mu_a$, scattering coefficient $\mu_s$ and/or anisotropy factor g of the sample from the measured reflectance image, and to estimate a size parameter of the embedded region based on the absorption coefficient $\mu_a$, scattering coefficient $\mu_s$ and/or anisotropy factor g of the sample from the measured reflectance image.

BRIEF DESCRIPTION OF THE DRAWINGS

The accompanying drawings, which are incorporated in and constitute a part of the specification, illustrate embodiments of the invention and, together with the description, serve to explain principles of the invention.

FIGS. 2a-2b are graphs of calculated reflectance images obtained through Monte Carlo simulations according to embodiments of the present invention for the effect of lens-sample distance h on reflectance image $R_c(0, y)$ for an incident beam having the profile shown in FIG. 1b. The lines in FIG. 2a represent the reflectance images calculated at different h along the y-axis with x=0 and the square symbols in FIG. 2a represent the profile obtained by multiplying $R_c(0, y)$ calculated at h=0.2 mm by a scaling constant S=1.86; and the symbols in FIG. 2b represent the h dependence of $R_c(0, -5$ mm). The simulation parameters for the data of FIGS. 2a-2b are as follows: $\mu_a=0.50$ mm$^{-1}$, $\mu_s=1.8$ mm$^{-1}$, g=0.60, lens diameter=18 mm, $N_l$ ranges between $2\times10^7$ and $2\times10^{11}$. The line in FIG. 2b is a visual guide.

FIGS. 3a-3d are contour plots of the squared error function $\delta$ in the parameter space of $\mu_t(=\mu_a+\mu_s)$, $a(=\mu_s/\mu_t)$ and g at $\mu_t=1.66$ mm$^{-1}$ (FIGS. 3a and 3b) and at a=0.76 (FIGS. 3c and 3d) for two profiles of a grating profile (FIGS. 3a and 3c) and a top-hat profile (FIGS. 3b and 3d) for the incident beam obtained with the reflectance image measured from the dark phantom sample at $\theta_0=45°$ and $\lambda=620$ nm according to embodiments of the present invention.

DETAILED DESCRIPTION OF EMBODIMENTS OF THE INVENTION

Figure 1A:
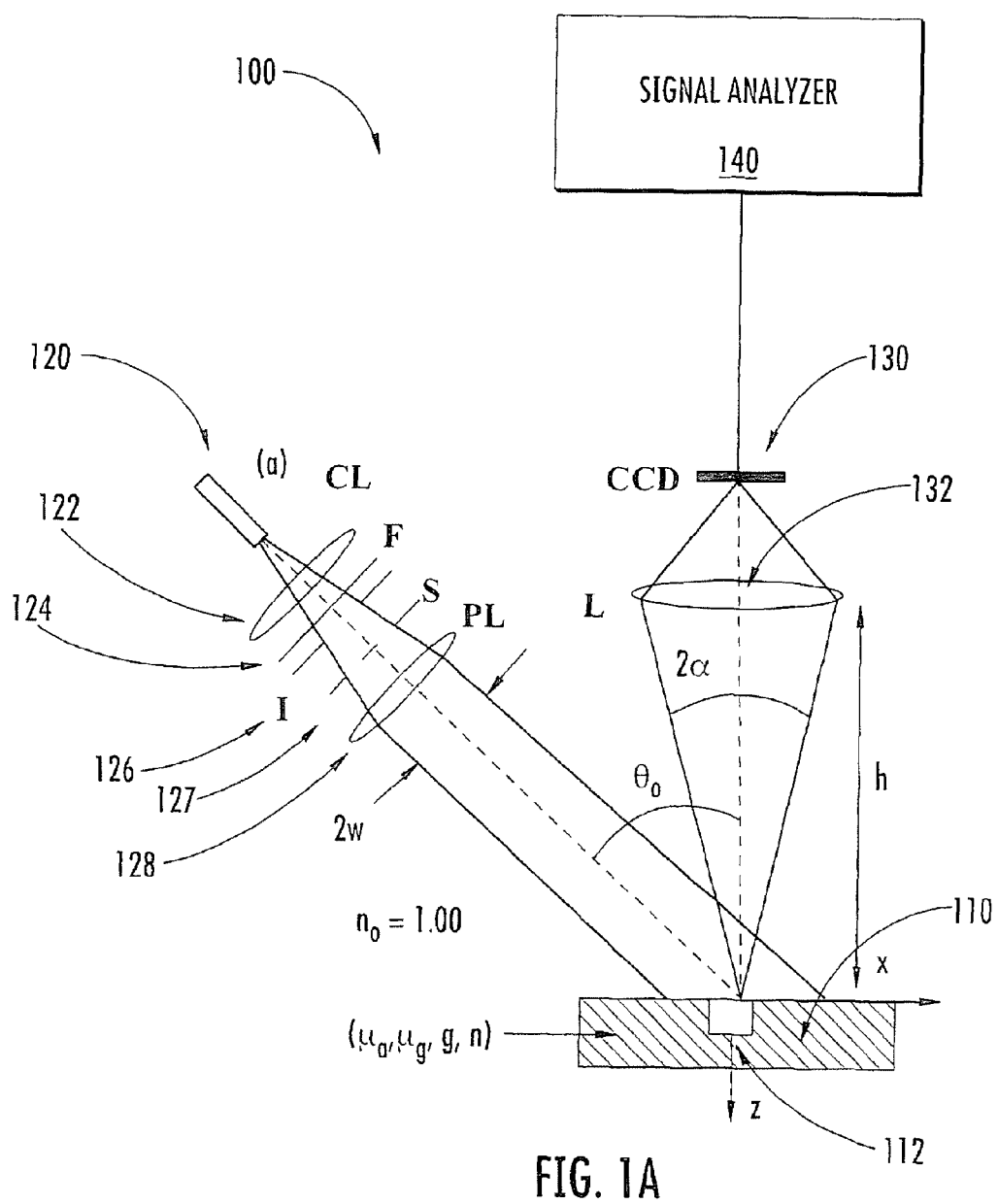
FIG. 1a is a schematic diagram of an imaging system (in which CL: condenser lens; F: wavelength filter; I: iris; S: stencil; PL: projection lens; L: camera lens) according to embodiments of the present invention.

The present invention now will be described hereinafter with reference to the accompanying drawings and examples, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning, that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under." The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present invention. The sequence of operations (or steps) is not limited to the order presented in the claims or figures unless specifically indicated otherwise.

The present invention is described below with reference to block diagrams and/or flowchart illustrations of methods, apparatus (systems) and/or computer program products according to embodiments of the invention. It is understood that each block of the block diagrams and/or flowchart illustrations, and combinations of blocks in the block diagrams and/or flowchart illustrations, can be implemented by computer program instructions. These computer program instructions may be provided to a processor of a general purpose computer, special purpose computer, and/or other programmable data processing apparatus to produce a machine, such that the instructions, which execute via the processor of the computer and/or other programmable data processing apparatus, create means for implementing the functions/acts specified in the block diagrams and/or flowchart block or blocks.

These computer program instructions may also be stored in a computer-readable memory that can direct a computer or other programmable data processing apparatus to function in a particular manner, such that the instructions stored in the computer-readable memory produce an article of manufacture including instructions which implement the function/act specified in the block diagrams and/or flowchart block or blocks.

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions/acts specified in the block diagrams and/or flowchart block or blocks.

Accordingly, the present invention may be embodied in hardware and/or in software (including firmware, resident software, micro-code, etc.). Furthermore, embodiments of the present invention may take the form of a computer program product on a computer-usable or computer-readable storage medium having computer-usable or computer-readable program code embodied in the medium for use by or in connection with an instruction execution system. In the context of this document, a computer-usable or computer-readable medium may be any medium that can contain or store the program for use by or in connection with the instruction execution system, apparatus, or device.

The computer-usable or computer-readable medium may be, for example but not limited to, an electronic, magnetic, optical, electromagnetic, infrared, or semiconductor system, apparatus or device. More specific examples (a non-exhaustive list) of the computer-readable medium would include the following: a portable computer diskette, a random access memory (RAM), a read-only memory (ROM), an erasable programmable read-only memory (EPROM or Flash memory), and a portable compact disc read-only memory (CD-ROM).

As illustrated in FIG. 1a, a system 100 for optically characterizing a turbid sample 110 includes an incoherent light source 120 for impinging a light beam, such as a structured, full-field light beam, on the sample 110 and an imaging detector 130 (such as a CCD detector) for detecting reflectance signals from the sample 110. The light source 120 can be a continuous wave, incoherent or coherent monochromatic light source. If coherent beams, such as a laser beam, are used, the "speckle effect" of interference patterns can be reduced using spatial averaging. As illustrated, the light beam from the light source 120 is passed through a condenser lens 122, a wavelength filter 124, an iris 126, a stencil 127 and a projection lens 128 to produce a structured, incoherent and monochromatic light beam, for example, a Tungsten-Halogen lamp light source with an interference wavelength filter. In some embodiments, a laser beam can be used without requiring a wavelength selection device (i.e., a filter, grating or prism). If a coherent such as a laser beam is used, wavelength filtering may not be needed. The sample 110 can be a heterogeneous sample that includes at least one embedded region 112. The embedded region 112 has material properties or optical parameters that are different from the other regions of the sample and can cause different reflected light signals than a homogeneous sample without the embedded region 112. The reflected light from the sample 110 passes through a camera lens 132 and is detected by the imaging detector 130. The detected reflected light signals are analyzed by a signal analyzer 140. In this configuration, the detector 130 is spaced-apart from the sample 110, and direct contact from a probe, such as an optical fiber, is not required.

Figure 1B:
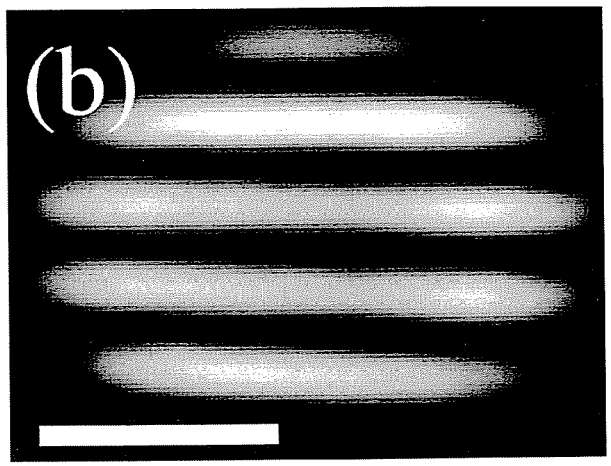
FIG. 1b is a digital profile image of a beam with a grating profile from a diffuse reflectance standard acquired with incident angle $\theta_0=45°$, $\lambda=620$ nm, bar=10 mm according to embodiments of the present invention.
Figure 1C:
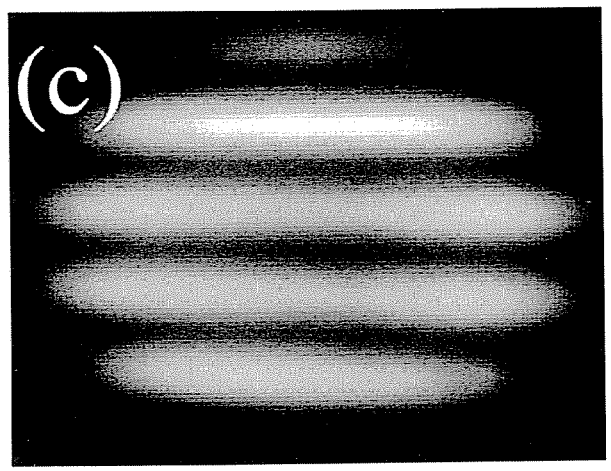
FIG. 1c is a digital reflectance image of the beam of FIG. 1b from a dark sample acquired with incident angle $\theta_0=45°$, $\lambda=620$ nm, bar=10 mm according, to embodiments of the present invention.
Figure 1D:
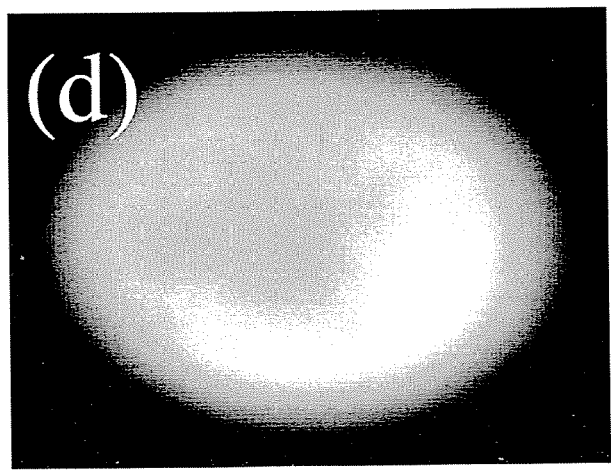
FIG. 1d is a digital profile image of a beam with a top-hat profile acquired with incident angle $\theta_0=45°$, $\lambda=620$ nm, bar=10 mm according to embodiments of the present invention.

The stencil 127 includes transmissive and non-transmissive regions such that the light exiting the stencil 127 is a structured light beam, i.e., a light beam having a pattern of bright and dark regions. Exemplary digital images of light beam images are shown in FIGS. 1b-1d. For example, FIG. 1b is a digital profile image of a beam with a grating profile from a diffuse reflectance standard acquired with incident angle $\theta_0=45°$, $\lambda=620$ nm, bar=10 mm. FIG. 1c is a digital reflectance image of the beam of FIG. 1b from a dark sample acquired with incident angle $\theta_0=45°$, $\lambda=620$ nm, bar=10 mm. FIG. 1d is a digital profile image of a beam with top-hat profile acquired with incident angle $\theta_0=45°$, $\lambda=620$ nm, bar=10 mm according to embodiments of the present invention. As used herein, a "top-hat" profile refers to a beam profile in which the light intensity decreases monotonically from a maximum-intensity point toward the peripheral of the profile.

Figure 1E:
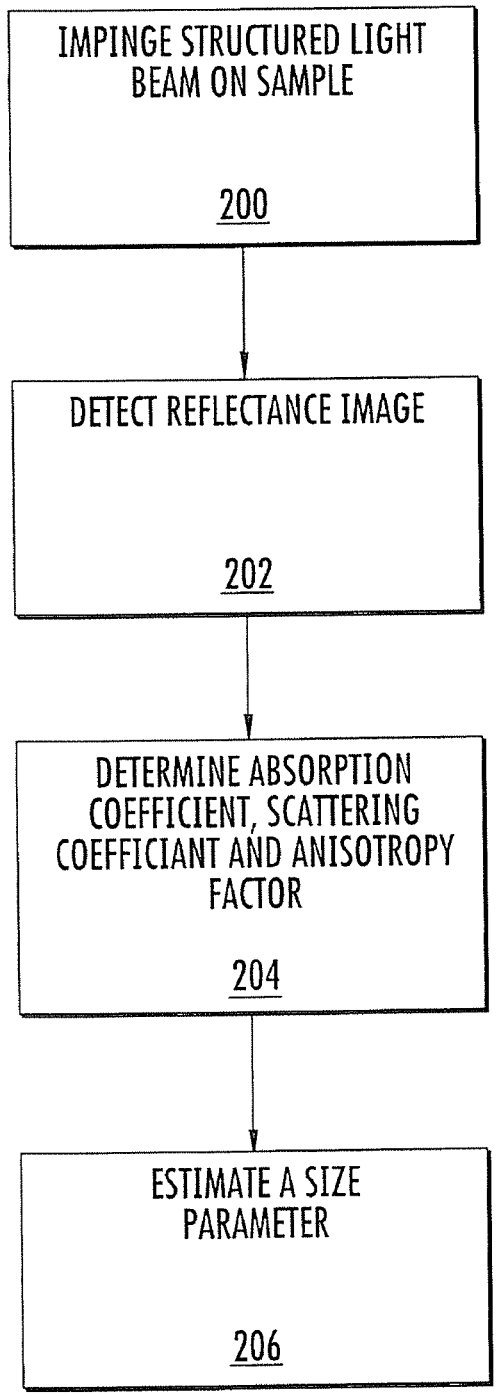
FIG. 1e is a flowchart illustrating operations according to embodiments of the present invention.
Figures 4A, 4B, 4C, 4D:
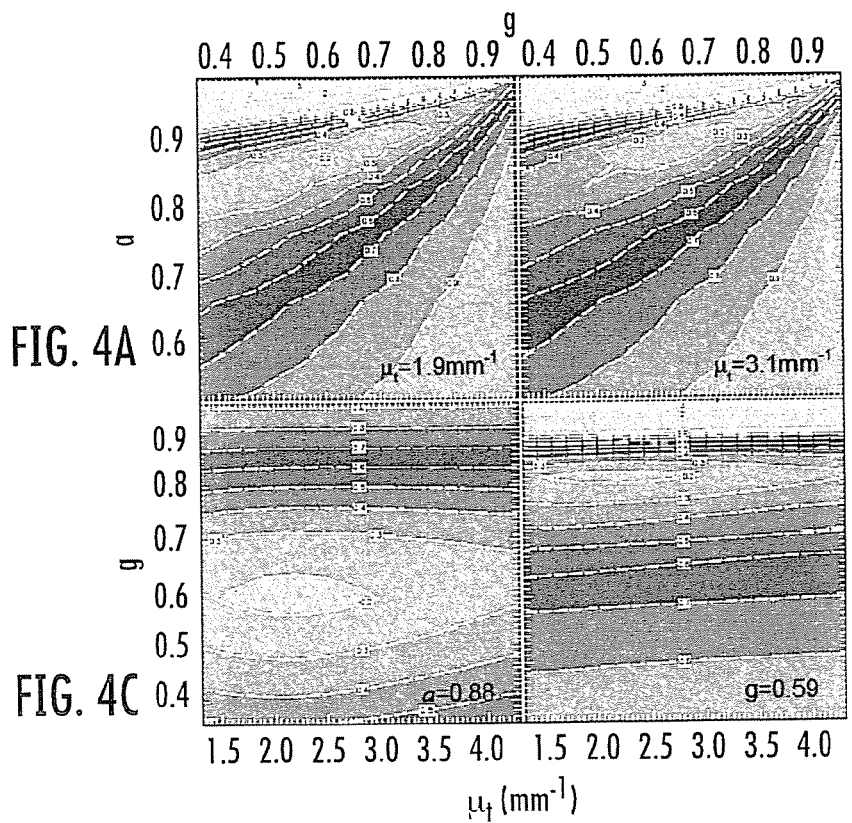
FIGS. 4a-4d are contour plots of the squared error function $\delta$ in the parameter space obtained with the reflectance image measured from the light phantom sample with an incident beam of grating profile at $\theta_0=45°$ and $\lambda=500$ nm according to embodiments of the present invention.

As illustrated in FIG. 1e, the structured light beam can be impinged on a sample (Block 200) by the light source 120 of FIG. 1a, and the reflectance image is detected (Block 202) by the detector 130 of FIG. 1a. The signal analyzer 140 of FIG. 1a is configured to determine the following parameters: absorption coefficient $\mu_a$, scattering coefficient $\mu_s$ and anisotropy factor g of the sample based on the reflectance image data detected by the detector 130 (Block 204). It should be understood that certain samples, such as heterogeneous samples, may be analyzed such that a plurality of absorption coefficients, scattering coefficients, and anisotropy factors are determined using the techniques described herein. A size parameter of the embedded region is estimated based on the absorption coefficient $\mu_a$, scattering coefficient $\mu_s$ and anisotropy factor g of the sample from the reflectance image (Block 206). In some embodiments, determining the absorption coefficients $\mu_a$, scattering coefficient $\mu_s$ and/or anisotropy factor g of the sample from the reflectance image is based on a calibration of the first reflected light image from the sample and a second reflected light image from a diffuse reflectance standard. Both reflected light images can be illuminated by the same structured light beam, such as an incoherent, full-field light beam. In some embodiments, determining the absorption coefficients $\mu_a$, scattering coefficient $\mu_s$ and anisotropy factor g of the sample from the reflectance image is based on a Monte Carlo simulation method using a single-parameter scattering phase function (see Henyey and Greenstein (21)). In some embodiments, determining the absorption coefficients $\mu_a$, scattering coefficient $\mu_s$ and anisotropy factor g of the sample from the reflectance image is based on a combination of Monte Carlo simulation techniques and a diffusion model. The diffusion model can be used as a rapid modeling tool to reduce the simulation time for parameter determination.

As used herein, the optical parameters of $\mu_a$, $\mu_s$ and g are equivalent to $\mu_t$, a and g, where the attenuation coefficient is $\mu_t=\mu_a+\mu_s$ and the single-scattering albedo is $a=\mu_s/\mu_t$. Therefore, $\mu_a$, $\mu_s$ and g are used interchangeably with $\mu_t$, a and g.

The determination of optical parameters of $\mu_a$, $\mu_s$ and g from the measured reflectance image is performed in the form of an iteration process in which a calculated reflectance image is obtained by the Monte Carlo simulation and compared to the measured reflectance image. A squared error function $\delta$ is defined as the relative errors between corresponding pixels in the calculated and measured images averaged over all the image pixels. If the optical parameters are not chosen correctly in the Mote Carlo simulation, the value of $\delta$ increases or remains large. The iteration process is guided by the principle to find an optimized set of parameter values so $\delta$ reaches a minimum value. In comparison to the smooth profiles such as the top-hat profile, the use of a structured profile such as the grating profile for the incident beam has the advantages of significantly increased speed of iterated simulations and accuracy of the optical parameters, as illustrated in FIG. 3. There are several reasons for the increased speed and accuracy of the simulations. First, the grating profile contains large variation of light intensity within the field of illumination and field of view by the imaging detector. Consequently, slight changes of optical parameters in the Monte Carlo simulation can lead to a large change in $\delta$. The high sensitivity of $\delta$ is advantageous to complete the iteration process since the correct values of optical parameters in the simulation can induce a large decrease in $\delta$ in comparison to the use of top-hat profile. Another potential benefit is that the photons that need to be tracked in the Monte Carlo simulation of a sample illuminated with a grating profile are fewer than the case with a top-hat profile because of the numerous dark regions in the grating profile. This may lead to a faster simulation and iteration processes.

In some embodiments, the embedded region comprises a tissue abnormality, and the size parameter of the embedded region is correlated to a likelihood of cancer malignancy. The tissue abnormality can be an epithelial abnormality, and the size parameter is a depth of the epithelial abnormality. Accordingly, embodiments of the invention can be used to estimate a depth/size of a cancerous or pre-cancerous epithelial growth. The depth of an epithelial growth can be an important factor in determining a lesion stage for diagnosis, for example, for melanoma and other skin cancers. For example, the depth of an epithelial growth can be correlated with whether the growth is a hyperplasia growth, a dysplasia growth, in situ cancer (i.e., that has not penetrated outside of the epithelial layer) or an invasive cancer (i.e., that has potentially penetrated into the tissue below the epithelial layer). Thus, the determination of the size parameters can be useful for a non-invasive, optical biopsy of an epithelial growth.

Although embodiments according, to the present invention are described herein with respect to epithelial cancerous or pre-cancerous growths, it should be understood that any suitable sample could be used which include connective and nerve tissues.

It should also be understood that multiple monochromatic light sources can also be used without the wavelength filters to vary the wavelength of the incident light beam. For example, in addition to the use of size parameters for diagnosis, the wavelength dependence of the optical parameters $\mu_a$, $\mu_s$ and g can be determined by varying the wavelength of monochromatic incident light beams. The wavelength dependence of the optical parameters $\mu_a$, $\mu_s$ and g can be used to differentiate legion types, for example, by applying a multivariate analysis method to multispectral imaging data.

In some embodiments, the turbidity of the sample 110 and/or the region 112 is related to the fact that its scattering coefficient $\mu_s$ is at least 0.1 mm$^{-1}$.

Embodiments according to the present invention will now be described with respect to the following, non-limiting examples.

EXAMPLES

A continuous-wave reflectance imaging method to determine absorption coefficients $\mu_a$, scattering coefficient $\mu_s$ and anisotropy factor g of a homogeneous turbid sample from a reflectance image was developed and validated. A parallel Monte Carlo ("MC") method was used to accurately model the reflectance image data and a mapping technique was developed to increase the simulation speed. By calibration of a full-field illumination with an incoherent beam of structured profile, the existence of a unique solution for the inverse problem was proven and the optical parameters of two tissue phantom samples between 500 and 950 nm was determined. The reflectance imaging method was further extended to determine the thickness of an embedded region in heterogeneous tissue phantom samples. With these results, it was demonstrated that the reflectance imaging method provides an experimentally simple means to quantitatively characterize turbid media with a multispectral capacity.

As used herein, a quantitative characterization is a determination of optical model-based parameters instead of those defined solely through, e.g., texture, morphometric or statistical analysis of image data. A radiative transfer (RT) theory, originated from the treatment of light transport in the atmosphere (4), provides a widely accepted optical model for light distribution in and out of turbid media (5). In addition to the coefficients of absorption ($\mu_a$) and scattering, ($\mu_s$), the RT theory defines a scattering phase function p(s, s') for description of light scattered from a direction s to another s' to quantitatively characterize a turbid sample. In the simple cases such as suspensions of spheres and red blood cells, these parameters can be obtained from the coherent treatment of light scattering based on the Maxwell equations if the microscopic heterogeneity of refractive index is known (6, 7). This feature assures the RT theory as an accurate optical model of turbid medium that can be linked to the first principles.

For complex turbid media including the biological tissues, a single-parameter function p(cos Θ) proposed by Henyey-Greenstein with cos Θ=s·s' is often employed as an angularly averaged scattering phase function and the single parameter is given by the anisotropy factor g defined as follows:

$$\int_{4\pi} p(\cos\Theta)\cos\Theta d\Omega$$

Therefore, optical characterization of a homogeneous tissue phantom sample can be defined as an inverse problem to determine $\mu_a$, $\mu_s$, and g if the refractive index n is known. While boundary-value problems defined with the RT equation and appropriate boundary conditions can be solved numerically, a statistical method of Monte Carlo (MC) simulation often serves as an alternative method to calculate light distribution for its simplicity in technique (9-11). The disadvantage of the MC simulation method is the high computing cost for variance reduction. For light distributions dominated by multiply scattered light, various diffusion approximations to the RT equation have been proposed to obtain closed-form or numerical solutions using two parameters of $\mu_a$ and a reduced scattering coefficient $\mu_s'=\mu_s(1-g)$ (5). Recently, the validity of a diffusion solution was investigated to model the reflectance images with full-field illumination and showed that the modeling accuracy decreases for samples of small single-scattering albedo a ($=\mu_s/\mu_t$) and/or large g (12).

A continuous-wave reflectance imaging method was developed that incorporates a full-field incoherent illumination, accurate calibration and rapid MC simulations for extraction of $\mu_a$, $\mu_s$ and g of homogeneous tissue phantom samples. The landscape of an objective function in the parameter space has been investigated to examine the uniqueness of the inverse solution and its dependence on the incident beam profile. The optical parameters of two phantom samples have been determined between 500 and 950 nm in wavelength and compared to those by an established method of integrating sphere to evaluate the reflectance imaging method. The same method was applied to determine the thickness of an embedded region in heterogeneous tissue phantom samples to illustrate its potentials for noninvasive staging of pigmented lesions in the skin.

Results

Rapid Modeling of Reflectance Images

For inverse determination of optical parameters of the homogeneous samples, a parallel MC code was developed and validated to simulate reflectance image in an imaging configuration shown in FIG. 1a (21). At the experimental value of the lens-sample distance h=400 mm, direct simulation of a reflectance image $R_c(x, y; h)$ requires tracking $2 \times 10^{11}$ or more photons to make variance negligible because of the very small cone angle to collect reflected photons. Even with parallel computing, tracking such a large number of photons can take days to obtain just one image. Techniques for significantly reducing the time for the MC simulations may be useful. The h dependence of $R_c$ for incident beams of both grating and top-hat profiles shown in FIGS. 1b and 1d was studied. It was found that for h>100 mm the reflectance image profile itself becomes independent of h while the reflectance value increases monotonically with h for both profiles. FIG. 2b displays the dependence of $R_c$ at a peak location of x=0 and y=−5.0 mm for the grating profile which shows $R_c$ approaching different asymptotic values as h approaches zero and h>100 mm. This allows the definition of a scaling constant $S=R_c(x, y; h)/R_c(x, y; 0)$ which can be used to obtain $R_c$ at h=400 mm from the $R_c$ calculated at h=0. FIG. 2a presents one example with S evaluated at x=0 and y=−5.0 mm. The dependence of S on the optical parameters of $\mu_a$, $\mu_s$, g and n was studied numerically, and it was found that the relative change of its value was less than 5% in the parameter ranges concerned in this procedure. Based on these results, MC simulations of $R_c$ for the following analysis were carried out at h=0 and then mapped to h=400 mm using a scaling constant S=1.90 before being compared to the measured reflectance image $R_m$. This technique drastically reduces the required number of tracked photons by 4 orders of magnitude to $3 \times 10^7$, and thus reduces the computational cost. For the parallel MC code executed on a computing cluster of 30 Intel Xeon CPUs of 3 GHz, the computational time of $R_c$ are 1.6 s and 34 s with values of ($\mu_a$, $\mu_s$, g) of (0.64 mm$^{-1}$, 0.66 mm$^{-1}$, 0.96) and (0.0088 mm$^{-1}$, 1.29 mm$^{-1}$, 0.36), respectively. The mapping technique described above is one key innovation that enables the rapid MC simulation of reflectance images and allows the investigation of the landscape of the parameter space consisting of $\mu_t$, a and g within days. The attenuation coefficient is $\mu_t=\mu_a+\mu_s$ and the single-scattering albedo is $a=\mu_s/\mu_t$.

Effect of Beam Profile on the Inverse Problem Solution

One reflectance image from a diffuse reflectance standard can be used for calibration of both measured and calculated images for a phantom sample. This approach can reduce the errors if the real distribution of incident light has to be approximated with analytical functions, and thus allows the study of structured incident beam profiles to keep the inverse problem from becoming ill-conditioned. The inverse problem of extracting optical parameters of a homogeneous turbid sample from the measured image $R_m(x, y; \lambda)$ is defined herein as a search for the minimum value of a squared error function δ in the parameter space of $\mu_t$, a and g at given λ between 500 and 950 nm and n=1.40. For this purpose, the squared error function δ is defined in the following as the mean relative error per pixel between the measured and calculated reflectance images $$\delta = \sqrt{\frac{1}{N_p}\sum_{x,y} H(x, y)\left|\frac{R_m(x, y; \lambda) - R_c(x, y; h)}{R_m(x, y; \lambda)}\right|^2}. \quad (1)$$

where the sum is taken over all pixels located at sample surface plane of (x, y) with a weighing factor H and $N_p$ is the total number of pixels with H=1. The factor H is set to 0 if the pixel value of $R_m$ is less than 5% of the maximum pixel value and 1 otherwise to exclude those pixels of large noises. The excluded pixels are those in the peripheral of the field-of-view (FOV) because of low incident irradiance.

The effect of incident beam profiles on the functional form of δ or landscape in the parameter space with two profiles of grating and top-hat measured from the dark sample at $\theta_0=45°$ and $\lambda=620$ nm was investigated, as shown in FIGS. 1b and 1d. At each fixed value of $\mu_t$, about 200 images were calculated with different values of a and g to obtain a contour plot of δ relative to the measured image. After study with different $\mu_t$, a single minimum of δ exists in the parameter space for both beam profiles, and FIGS. 3a-3d present two contour plots for each profile at the optimized $\mu_t$ or a. As can be seen from FIGS. 3a-3d, the grating profile produces a slightly steeper slope for δ to descend to its minimum and the parameter values obtained there are closer to the values determined by the integrating sphere based method. The advantage of a grating profile over the top-hat profile can be attributed to the larger variation in the reflectance values which makes δ more sensitive to the parameter change. For this reason, the grating profile was chosen for subsequent studies.

Determination of Optical Parameters for Homogeneous Samples

To develop reliable inverse techniques, the landscape in the parameter space for two tissue phantom samples of the light and dark appearance was investigated at selected wavelengths because of different concentrations of pigments. A preliminary search was first performed by combining a diffusion solution (12) and the MC method to find an initial set of $\mu_t$, a and g values. Then about 2000 reflectance images were calculated with about 12 steps along each parameter axis to generate multiple contour maps of δ in the parameter space. It was confirmed again that a unique minimum exists for δ for the surveyed ranges of the parameters, with typical contour plots shown in FIGS. 4a-4d for the light phantom sample. These results show that the sensitivity of δ on each parameter decreases in the order of a, g and $\mu_t$. Based on this information, a simple gradient-based search technique was adopted to determine the optical parameters of a sample between 500 and 950 nm after their values were found at the first wavelength through the contour plots. The technique uses a first scan a with a variable step size to reach an optimized value with g and $\mu_t$ fixed at the values determined at last wavelength, followed by repeating similar searches on g and $\mu_t$.

Figure 5:
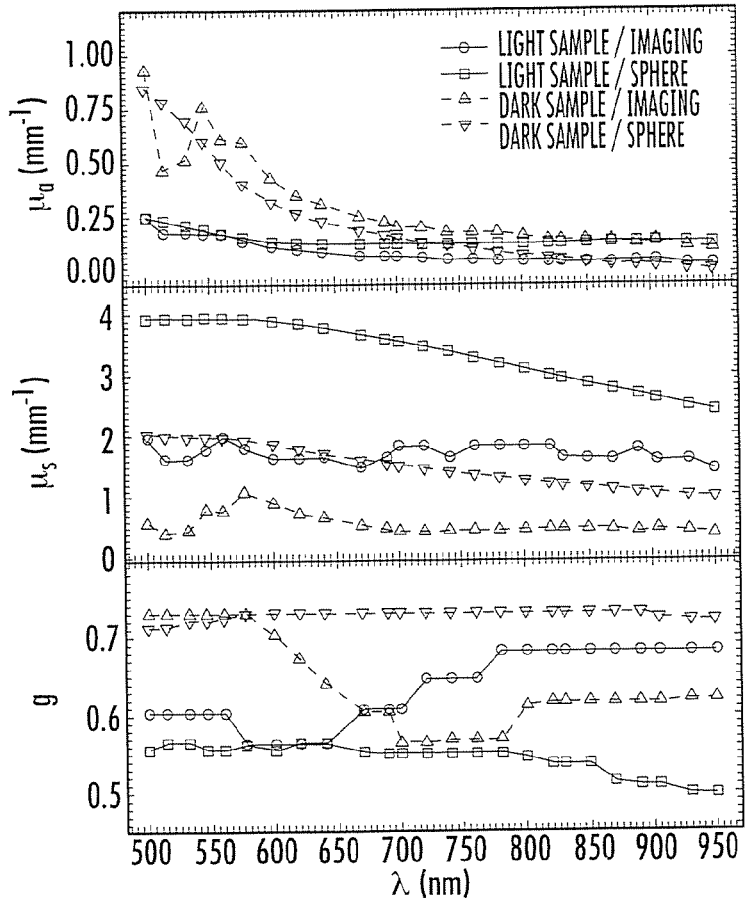
FIG. 5 is a graph of the wavelength dependence of absorption coefficient $\mu_a$, scattering coefficient $\mu_s$ and anisotropy factor g of dark and light phantom samples determined by reflectance imaging techniques and integrating sphere techniques according to embodiments of the present invention. The lines in FIG. 5 are for visual guide.

This procedure was repeated until the parameters converge to the same set of values. With this technique, it took about 2000 MC simulations to determine the parameters at the first wavelength and 100 simulations for each of the subsequent wavelengths for one sample. Local search was performed at selected wavelengths to confirm that the minimum value of δ is reached at the final parameter values. The optical parameters of the two homogeneous tissue phantom samples are presented in FIG. 5. FIG. 5 also contains the values of these parameters determined from the thin disk samples made with the same suspensions for each imaging phantom sample using an integrating sphere method. In this method, the collimated transmittance was first measured with four thin disks to determine $\mu_t$. This was followed by the measurement of diffuse reflectance and transmittance from one disk sample which was compared to calculated signals using a MC method to determine a and g (22).

Determination of Embedded Region Thickness in Heterogeneous Samples

Figure 6:
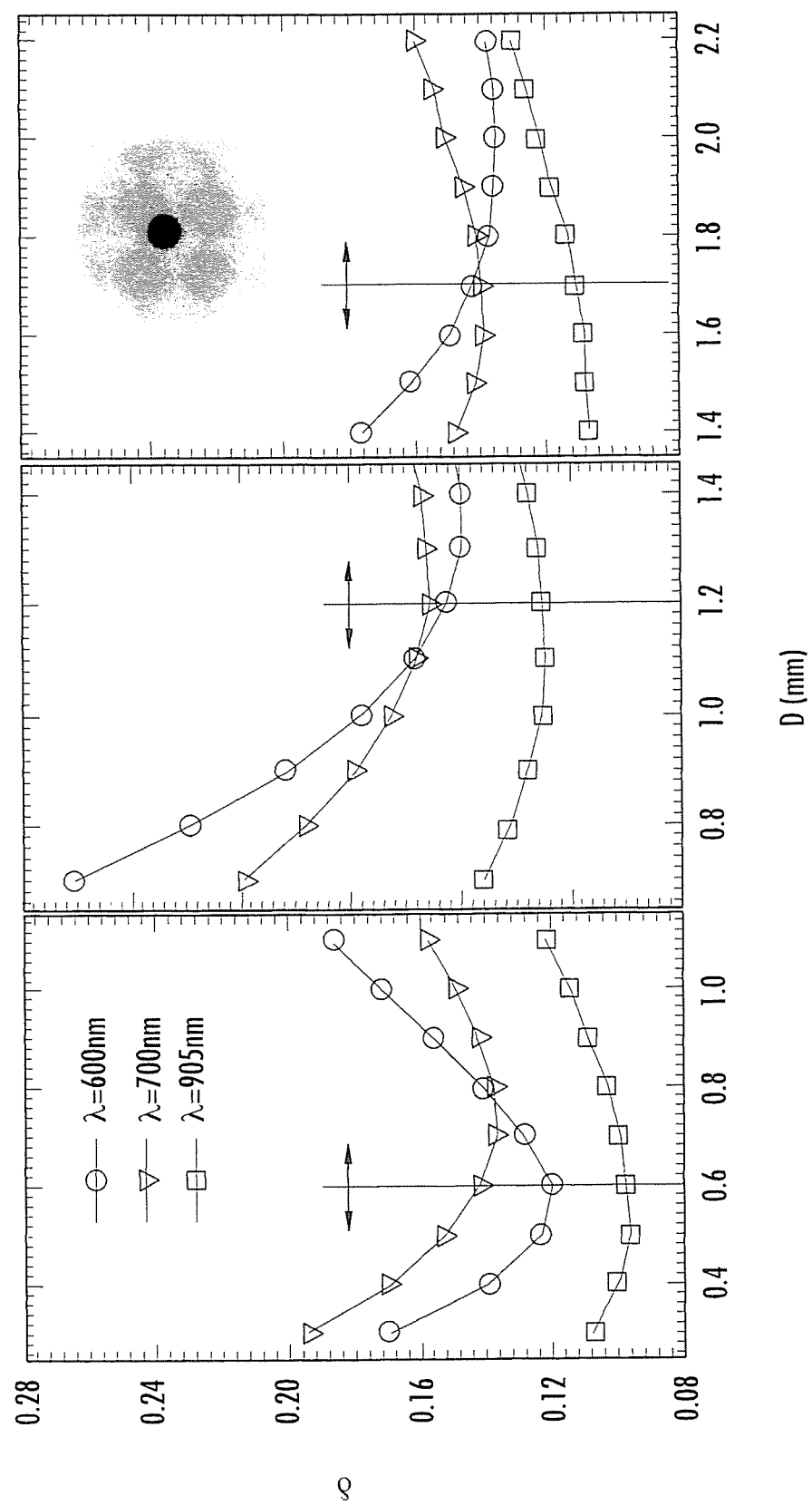
FIG. 6 is a graph of the objective function $\delta$ versus the thickness D (mm) of an embedded region in three heterogeneous phantom samples at different wavelengths according to embodiments of the present invention. The vertical lines and attached arrow lines indicate the measured thickness $D_m$ and uncertainty values. The inset is a photo of one sample and the lines are for visual guide.

One of potential applications for the reflectance imaging method described here is the noninvasive diagnosis and staging of superficial lesions such as malignant melanoma. In current melanoma staging system the Breslow's thickness or tumor thickness plays a central role, which can only be determined through examination of biopsied tissues (23). To illustrate this possibility, the reflectance imaging method on three heterogeneous tissue phantom samples was applied. These samples were made of two suspensions identical to those for the light and dark homogeneous phantom samples. The heterogeneous samples consist of a dark suspension filling a region of cylinder shape (8 mm in diameter and variable thickness D) at the center of the substrate (40 mm in diameter and 10 mm in thickness) with the light suspension, as shown by the photon in the inset of FIG. 6. The thickness of the embedded region was controlled to be $D_m=0.6$, 1.2 and 1.7±0.1 mm for each of the three samples with a molding insert. For each $R_m$ acquired at a selected wavelength, an image $R_c$ was calculated with the optical parameters presented in FIG. 5 for the two regions and a variable D for the embedded region to obtain a value of the function δ defined in Eq. (1). Then the dependence of δ on D was obtained in which the minimum of δ, shown in FIG. 6 for the three samples at different wavelengths, indicate the optical determined value of D.

Discussion

Light penetrating and emanating from a turbid sample in reflected directions carries rich information for optical characterization. A reflectance imaging method was developed to quantitatively characterize a homogeneous turbid sample on the basis of the RT theory, where the sample can be "non-diffusive" or of arbitrary values of a and g. The imaging method utilizes an incoherent continuous wavelength light source for full-field illumination of the sample at an oblique angle and is capable of determining $\mu_a$, $\mu_s$ and g of the sample from one reflectance image at a selected wavelength. The precise calibration of the measured and calculated reflectance images with a diffuse reflectance standard and development of an accurate and rapid MC method are used in forming a well-posted inverse problem, and a unique solution has been shown to exist in the parameter space of $\mu_t$, a and g for homogeneous samples. For validation, the optical parameters of two phantom samples were compared as determined by the reflectance imaging method with those of the thin disk samples determined by an integrating sphere based method. It can be seen from FIG. 5 that the two sets of parameters exhibit good agreement for $\mu_a$ and g at some wavelengths and large disagreement for $\mu_s$ and g at other wavelengths. While the difference in samples, prepared in different weeks, may be a reason for the disagreement, the disagreement can be attributed mainly to the simple inverse techniques used in this study, which may fail to reach the true minimum in δ with repeated single parameter search. The errors in the image measurement and modeling may also contribute to the disagreement. Currently, the Nelder-Mead simplex (24) and other gradient based methods are being investigated as the inverse techniques for improved accuracy of minimum search and speed of decent in δ. With an efficient inverse technique and implementation of parallel MC simulations on computing clusters of rapidly decreasing performance/price ratio, it is anticipated that the availability of a reflectance imaging system in the near future for determination of $\mu_a$, $\mu_s$ and g of an optically thick turbid sample at each wavelength within a few minutes and the parameter spectra within an hour. The technique can be easily extended to mid- and long-wave near-infrared and other spectral regions where imagers are readily available.

One significant application of the reflectance imaging method is to realize noninvasive optical biopsy for diagnosis and staging of lesions. Optical biopsy is attractive for its safety with non-ionizing radiation and capability of probing the superficial structures of optically thick tissues, complementary to the existing imaging modalities such as ultrasound and x-ray computed tomography. The potential for determination of the thickness of a pigmented lesion embedded in a tissue bed, such as the cutaneous melanoma, has been demonstrated. It is well known that the thickness and enlargement of a pigmented mole in the skin provides key indicators for the diagnosis of the malignant melanoma and patient's prognosis in either the Breslow's thickness or Clark's staging system (23). The results shown in FIG. 6 suggest the possibility of applying the reflectance imaging, method to directly determine the thickness if the optical parameters of the heterogeneous tissues are known. It is clear from FIG. 6 that the accuracy of D determining, depends on the accuracy of the optical parameters used in the $R_c$ calculations. Thus, an improved inverse technique for simultaneously determination of optical parameters and lesion thickness can significantly increase the accuracy of D determination. Further refinement of image acquisition, processing and inverse calculation may enable the reflectance imaging method with a multispectral capacity as a powerful means of optical biopsy.

Methods

An incident beam from a Tungsten-lamp light source was projected on the surface of a tissue phantom sample after passing, through an interference filter of 10 nm width at a selected wavelength λ followed by an iris and a stencil for generating a desired beam profile. The center axis of the incident beam intersects with sample surface at an incident angle of $\theta_0=45°$ with a diverging angle of 1.9°. FIG. 1a presents the experimental design and two incident beam profiles. Two types of phantom samples, with light and dark appearance, were made with TiO2 powders (213581000, Acros Organics) and different concentrations of brown pigment powders (Pbr7, Kama Pigments) suspended in silicone polymer (RTV615A, MG Chemicals). The suspensions were stirred during the sample casting, period of 1 week to ensure homogeneity before curing. Two homogeneous tissue phantom samples with light and dark appearance were used for this study with each molded as a cylinder of 40 mm in diameter and 10 mm in thickness. Multiple thin disk copies were made for each phantom sample out of the same suspension with 18 mm in diameter and 0.1 to 1 mm in thickness for integrating sphere based measurements (22).

A thermoelectrically cooled 16-bit CCD camera of 765×510 pixels (ST-7, SBIG) was oriented along, the normal direction of sample surface to acquire reflected light images in the x-y plane at the sample surface of z=0. A camera lens of 25 mm in focal length and 18 mm aperture diameter was used to acquire reflected light distribution, $I_{r0}(x, y; \lambda)$, from the sample. The imaging system was aligned so that the CCD sensor plane forms a conjugate relation with the z=0 plane with a lens-sample distance h. To calibrate the image data for accurate simulations, the same system was used to acquire an image $I_{s0}(x, y; \lambda)$ from a diffuse reflectance standard (Labsphere, Inc.) with calibrated reflectance value $R_s$ of 10% or 40% in the place of sample. This image was used to generate a measured reflectance image of the sample and a profile image of the incident beam for generating the calculated reflectance image. All images were cropped and pixel binned to produce an FOV of 25.5×19.4 mm² with 133×10[1] pixels. Separate background images of $I_{rb}(x, y)$ and $I_{sb}(x, y)$ from the sample and reflectance standard were obtained with the incident beam blocked. The background-free images, $I_i(x, y; \lambda)=I_{i0}(z, y; \lambda)-I_{ib}(x, y)$, with i=r or s, were used to construct a measured reflectance image as $$R_m(x, y; \lambda) = \frac{I_r(x, y; \lambda) R_s}{I_{max,s}} \quad (2)$$

and a normalized profile image of $$P(x, y; \lambda) = \frac{I_s(x, y; \lambda)}{I_{max,s}}$$

for the incident beam, where $I_{max,s}$ is the maximum pixel value of the image $I_s(x, y; \lambda)$. FIGS. 1b-1d present reflectance images from a diffuse reflectance standard of $R_s=10\%$ and one phantom sample of dark appearance.

A parallel MC code has been developed for this study to rapidly calculate reflectance images of a tissue phantom configuration shown in FIG. 1a with given optical parameters $\mu_a$, $\mu_s$, g, n and sample size parameters (21). For all simulations, n was a constant of 1.40, measured at λ=633 nm using a coherent reflectance method (25), since the variation of the refractive index n of the silicone based phantoms is very small and affects very little on the calculated images in the concerned spectral region (21). The MC simulation starts by launching photons with an incident photon density $\rho_i(x, y)$ at the air side of phantom surface (z=0) in a surface grid conformal with the FOV. The incident beam is represented by $N_i$ photons and majority of them, according to the Fresnel reflection coefficient, are injected into the phantom for tracking individually until they exit the phantom (11). A reflected photon density $\rho_r(x, y; h)$ was obtained by registration of those photons exiting at the air side of phantom surface toward the camera lens located at z=−h. Compared to conventional definition of reflectance (21, 26), two changes of imaging studies of turbid media were adopted. First, the measured profile image $P(x, y; \lambda)$ of the incident beam at $\theta_0$ and λ is imported into the computer code to generate $\rho_i(x, y; h)$ at each grid cell for image calculation. Second, another reflectance image $\rho_s(x, y; h)$ is obtained analytically from an ideal diffuse reflectance standard of 100% reflectance in the place of the phantom. Based on the definition of diffuse reflectance standards (27), $\rho_s(x, y)$ can be calculated as follows:

$$\rho_s(x, y; h) = \frac{\Delta\Omega(x, y; h)}{2\pi} \rho_i(x, y), \quad (3)$$

where $\Delta\Omega(x, y; h)$ is the solid angle subtended by the camera lens from the (x, y) location on the phantom surface and $2\pi$ is the solid angle of the upper hemisphere. The calculated reflectance image is then defined as $$R_c(x, y; h) = \frac{\rho_r(x, y; h)}{\rho_{max,s}} \quad (4)$$

and compiled at the end of simulation, where $\rho_{max,s}$ is the maximum density in $\rho_s(x, y; h)$. From the above definition, one can see that $R_c$ varies as a function of the lens-sample distance h and may exceed 1 if the number of the photons reflected from a phantom exceeds that from the ideal reflectance standard. It is noted that the reflectance defined in Eq. (4) returns back to the conventional definition of $R_c(x, y; 0) = \rho_r(x, y)/\rho_{max, i}$ (21) for h=0 since $\Delta\Omega(x, y; 0) = 2\pi$.

In some embodiments, the Monte Carlo techniques described above can include the following features to enable its use for efficient and accurate determination of the optical parameters. First, a mapping relation was discovered between the reflectance image calculated by assuming, the camera is very close to the sample (h~0 mm), and the image calculated by assuming the camera is at the actual distance from the sample (h=400 mm). See FIGS. 2a and 2b. With this mapping relation, the Monte Carlo simulation time can be reduced, e.g., in some embodiments, by a factor of 10,000 by first calculating a reflectance image with h set to 0 (which tracks only about $10^7$ photons) and then mapping, the reflectance image to the actual distance of h, such as h=400 mm (which, e.g., tracks only about $10^{11}$ photons) to obtain the calculated reflectance image that is comparable to the measured one. In addition, the second reflected light image from the diffuse reflectance standard can be used to decide the incident photon distribution in the Monte Carlo simulation (see Eqs. (3) and (4)), which can significantly increase the accuracy of calculated image in comparison to the measured image. This allows the iteration process to successfully stop at the unique minimum of the error function $\delta$. In other words, the high accuracy of calculated reflectance image by using the measured incident light beam profile from the reflectance standard may guaranty the uniqueness of the optical parameters as the output of the iteration process.

Although embodiments according to the present invention are described herein with respect to heterogeneous samples, it should be understood that homogeneous samples may also be used.

The foregoing is illustrative of the present invention and is not to be construed as limiting thereof. Although a few exemplary embodiments of this invention have been described, those skilled in the art will readily appreciate that many modifications are possible in the exemplary embodiments without materially departing, from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

REFERENCES

1. Perelman, L. T., Backman, V., Wallace, M., Zonios, G., Manoharan, R., Nusrat, A., Shields, S., Seiler, M., Lima, C., Hamann, T., et al. (1998) *Phys. Rev. Lett.* 80, 627-630.
2. Shah, N., Cerussi, A., Eker, C., Espinoza, J., Butler, J., Fishkin, J., Hornung, R., & Tromberg, B. (2001) *Proc Natl Acad Sci USA* 98, 4420-4425.
3. Torricelli, A., Pifferi, A., Spinelli, L., & Cubeddu, R. (2005) *Phys. Rev. Lett.* 95, 078101.
4. Chandrasekhar, S. (1950) *Radiative Transfer* (Oxford, Fair Lawn, N.J.).
5. Welch, A. J. & Gemert, M. J. C. v. (1995) *Optical-thermal response of laser-irradiated tissue* (Plenum Press, New York).
6. Ma, X., Lu, J. Q., Brock, R. S., Jacobs, K. M., Yang, P., & Hu, X. H. (2003) *Phys. Med. Biol.* 48, 4165-4172.
7. Lu, J. Q., Yang, P., & Hu, X. H. (2005) *J. Biomed. Opt.* 10, 024022.
8. Henyey, L. G. & Greenstein, J. L. (1941) *Astrophys J* 93, 70-83.
9. Wilson, B. C. & Adam, G. (1983) *Medical physics* 10, 824-830.
10. Wang, L., Jacques, S. L., & Zheng, L. (1995) *Comput Methods Programs Biomed* 47, 131-146.
11. Song, Z., Dong, K., Hu, X. H., & Lu, J. Q. (1999) *Appl. Opt.* 38, 2944-2949.
12. Lu, J. Q., Chen, C., Pravica, D. W., Brock, R. S., & Hu, X. H. (2008) *Med. Phys.* 35, 3979-3987.
13. Farrell, T. J., Patterson, M. S., & Wilson, B. (1992) *Medical physics* 19, 879-888.
14. Haskell, R. C., Svaasand, L. O., Tsay, T.-T., Feng, T.-C., McAdams, M. S., & Tromberg, B. J. (1994) *J. Opt. Soc. Am. A* 11, 2727-2741.
15. Fishkin, J. B., Fantini, S., vandeVen, M. J., & Gratton, E. (1996) *Phys. Rev. E* 53, 2307-2319.
16. Doornbos, R. M., Lang, R., Aalders, M. C., Cross, F. W., & Sterenborg, H. J. (1999) *Physics in medicine and biology* 44, 967-981.
17. Kienle, A., Lilge, L., Patterson, M. S., Hibst, R., Steiner, R., & Wilson, B. C. (1996) *Appl. Opt.* 35, 2304-2314.
18. Gobin, L., Blanchot, L., & Saint-Jalmes, H. (1999) *Applied optics* 38, 4217-4227.
19. Gurfinkel, M., Pan, T., & Sevick-Muraca, E. M. (2004) *Journal of biomedical optics* 9, 1336-1346.
20. Joshi, N., Donner, C., & Jensen, H. W. (2006) *Opt. Lett.* 31, 936-938.
21. Chen, C., Lu, J. Q., Li, K., Zhao, S., Brock, R. S., & Hu, X. H. (2007) *Med. Phys.* 34, 2939-2948
22. Chen, C., Lu, J. Q., Ding, H., Jacobs, K. M., Du, Y., & Hu, X. H. (2006) *Opt. Express* 14, 7420-7435.
23. Balch, C. M., Sober, A. J., Soong, S. J., & Gershenwald, J. E. (2003) *Semin. Cutan. Med Surg.* 22, 42-54.
24. Nelder, J. A. & Mead, R. (1965) *Comput. J.* 7, 308-313.
25. Ding, H., Lu, J. Q., Jacobs, K. M., & Hu, X. H. (2005) *J. Opt. Soc. Am. A* 22, 1151-1157.
26. Kortum, G. (1969) *Reflectance spectroscopy. Principles, methods, applications* (Springer, Berlin, Heidelberg, N.Y.).
27. Weidner, V. R. & Hsia, J. J. (1981) *J. Opt. Soc. Am.* 71, 856-861.

That which is claimed is:

1. A method for optically characterizing a turbid sample, the method comprising:
  impinging a structured light beam on the sample, wherein the sample comprises an embedded region;
  detecting a reflected light image of the structured light beam from the sample; determining a measured reflectance image of the structured light beam for the sample based on the reflected light image and a reflectance standard;

determining an absorption coefficient $\mu_a$, a scattering coefficient $\mu_s$, and/or an anisotropy factor g of the sample from the reflectance image;

estimating a size parameter of the embedded region based on the absorption coefficients $\mu_a$, scattering coefficient $\mu_s$ and/or anisotropy factor g of the sample from the measured reflectance image;

wherein determining a measured reflectance image comprises the reflected light image of the sample normalized by a reflected light image of the reflectance standard; and wherein the reflectance standard is a calibrated diffuse reflectance standard.

2. The method of claim 1, wherein the light beam is an incoherent, full-field light beam.

3. The method of claim 1, wherein the embedded region comprises a tissue abnormality, and the size parameter of the embedded region is correlated to a likelihood of cancer malignancy.

4. The method of claim 3, wherein the tissue abnormality comprises an epithelial abnormality, and the size parameter is a depth of the epithelial abnormality.

5. The method of claim 1, wherein the structured light beam is formed by passing an incoherent light beam through a stencil having transmissive and non-transmissive or partially transmissive regions to thereby form a structured profile.

6. The method of claim 5, wherein the structured profile is a grating pattern.

7. The method of claim 1, wherein the measured reflectance image is detected by a detector that is spaced-apart from the sample.

8. The method of claim 1, wherein the absorption coefficient $\mu_a$, scattering coefficient $\mu_s$ and/or anisotropy factor g of the sample from the refectance image is based on Monte Carlo simulation on the basis of radiative transfer theory.

9. The method of claim 8, wherein determining the absorption coefficient $\mu_a$, scattering coefficient $\mu_s$ and/or anisotropy factor g of the sample from the reflectance image is further based on an optical diffusion model.

10. A system for optically characterizing a turbid sample, the system comprising:

a structured light beam source configured to impinge a beam on a sample, wherein the sample comprises an embedded region;

a detector configured to detect a reflected light image of the structured light beam from the sample;

a signal analyzer configured to determine a measured reflectance image of the structured light beam for the sample based on the reflected light image of the sample normalized by another reflected light image of the reflectance standard, and to determine an absorption coefficient $\mu_a$, scattering coefficient $\mu_s$, and anisotropy factor g of the sample from the measured reflectance image, to estimate a size parameter of the embedded region based on the absorption coefficients $\mu_a$, scattering coefficient $\mu_s$, and/or anisotropy factor g of the sample from the measured reflectance image;

wherein the signal analyzer is further configured to determine a measured reflectance image by normalizing the reflected light image of the sample by the reflected light image of the reflectance standard; and wherein the reflectance standard is a calibrated diffuse reflectance standard.

11. The system of claim 10, wherein the light beam source is configured to provide an incoherent, full-field light beam.

12. The system of claim 10, wherein the embedded region comprises a tissue abnormality, and the signal analyzer is configured to correlate the size parameter of the embedded region to a likelihood of cancer malignancy.

13. The system of claim 12, wherein the tissue abnormality comprises an epithelial abnormality, and the size parameter is a depth of the epithelial abnormality.

14. The system of claim 10, wherein the incoherent light beam source further comprises a stencil having transmissive and non-transmissive or partially transmissive regions to thereby form a structured profile.

15. The system of claim 14, wherein the structured profile is a grating pattern.

16. The system of claim 10, wherein the detector is spaced-apart from the sample.

17. The system of claim 10, wherein the signal analyzer is configured to determine the absorption coefficient $\mu_a$, scattering coefficient $\mu_s$ and/or anisotropy factor g of the sample from the reflectance image based on a Monte Carlo simulation on the basis of radiative transfer theory.

18. The system of claim 17, wherein the signal analyzer is configured to determine the following: absorption coefficients $\mu_a$, reduced scattering coefficient $\mu_s'$ of the sample from the reflectance image based on an optical diffusion model.

19. A method for optically characterizing a turbid, biological tissue sample, the method comprising:

impinging a structured light beam on the tissue sample, wherein the tissue sample comprises an embedded region;

detecting a reflected light image of the structured light beam from the tissue sample;

determining a measured reflectance image of the structured light beam for the tissue sample based on the reflected light image of the sample normalized by a reflected light image of the reflectance standard, wherein the reflectance standard is a calibrated diffuse reflectance standard;

determining an absorption coefficient $\mu_a$, a scattering coefficient $\mu_s$, and/or an anisotropy factor g of the tissue sample from the reflectance image;

estimating a size parameter of the embedded region based on the absorption coefficients $\mu_a$, scattering coefficient $\mu_s$, and/or anisotropy factor g of the tissue sample from the measured reflectance image; and assessing a health parameter of the tissue sample based on the size parameter of the embedded region.

* * * * *

UNITED STATES PATENT AND TRADEMARK OFFICE
CERTIFICATE OF CORRECTION

| | | |
|---|---|---|
| PATENT NO. | : 8,634,077 B2 | Page 1 of 1 |
| APPLICATION NO. | : 13/122062 | |
| DATED | : January 21, 2014 | |
| INVENTOR(S) | : Hu et al. | |

It is certified that error appears in the above-identified patent and that said Letters Patent is hereby corrected as shown below:

On Title Page:
Item 57, Abstract, Lines 7-13: Please correct "The following parameters are determined: absorption coefficients ÿa, scattering coefficient ÿs and anisotropy factor g of the sample from the reflectance image. A size parameter of the embedded region is estimated based on the absorption coefficients ÿa, scattering coefficient ÿs and/or anisotropy factor g of the sample from the measured reflectance image."

to read -- The following parameters are determined: absorption coefficients $\mu_a$, scattering coefficient $\mu_s$ and anisotropy factor g of the sample from the reflectance image. A size parameter of the embedded region is estimated based on the absorption coefficients $\mu_a$, scattering coefficient $\mu_s$ and/or anisotropy factor g of the sample from the measured reflectance image. --

In the Claims:
Column 17, Line 36, Claim 8: Please correct "is based on Monte" to read -- is based on a Monte --

Signed and Sealed this
Twenty-first Day of April, 2015

Michelle K. Lee
*Director of the United States Patent and Trademark Office*